US012564521B2

(12) United States Patent
Clayborne et al.

(10) Patent No.: US 12,564,521 B2
(45) Date of Patent: Mar. 3, 2026

(54) NASAL COMPRESSION DEVICE

(71) Applicant: NASACLIP, INC., Baltimore, MD (US)

(72) Inventors: Elizabeth P. Clayborne, Laurel, MD (US); Neal Sikka, Vienna, VA (US); Romil Patel, Jamestown, RI (US)

(73) Assignee: NASACLIP, INC., Baltimore, MD (US)

( * ) Notice: Subject to any disclaimer, the term of this patent is extended or adjusted under 35 U.S.C. 154(b) by 321 days.

(21) Appl. No.: 18/124,340

(22) Filed: Mar. 21, 2023

(65) Prior Publication Data

US 2023/0301839 A1    Sep. 28, 2023

Related U.S. Application Data

(60) Provisional application No. 63/322,438, filed on Mar. 22, 2022.

(51) Int. Cl.
A61F 13/12        (2006.01)
A61F 13/00        (2024.01)
A61F 13/15        (2006.01)

(52) U.S. Cl.
CPC ........... A61F 13/126 (2013.01); A61F 13/15 (2013.01); A61F 2013/0028 (2013.01); A61F 2013/00285 (2013.01)

(58) Field of Classification Search
CPC .............. A61B 17/12104; A61B 17/24; A61B 17/1227; A61B 2017/12004; A62B 9/06;
(Continued)

(56) References Cited

U.S. PATENT DOCUMENTS 598,467  A      2/1898   Carence
675,275  A      5/1901   Gunning
(Continued)

FOREIGN PATENT DOCUMENTS

CN        201415010       *   3/2010
CN        301381375  S       11/2010
(Continued)

OTHER PUBLICATIONS

"100 Pieces Nose Plug Filter Disposable Nose Dust Filters Nostril Filters Spray Nose Filter Sponge Nose Plugs for Women Men Sunless Spray Tanning Outdoor Dust Construction Areas https://www.amazon.com/Disposable-Filters-Nostril-Sunless-Construction/dp/B09F9NN9ZH/%3C"., (Year: 2021).*
(Continued)

*Primary Examiner* — Ariana Zimbouski
*Assistant Examiner* — Matthew Wrubleski
(74) *Attorney, Agent, or Firm* — BLANK ROME LLP

(57)        ABSTRACT

A nose compression device to treat a nosebleed. The device has a wire frame with a straight middle section and two side sections angled with respect to the middle section to apply an inward compression against an outside of the person's nose. The device also includes a support member attached to the wire frame. And, a single nasal sponge attached to the body and having a central sponge portion and two opposing sponge end portions, each of said two opposing sponge end portions configured for insertion into the person's nasal passages.

22 Claims, 4 Drawing Sheets

(58) Field of Classification Search
CPC .......... A61M 2210/0618; A61F 13/126; A61F 13/2005; A61F 2007/00026; A61F 13/15; A61F 2013/0028; A61F 2013/00285; A61F 2013/00476; A61F 13/20
See application file for complete search history.

(56) References Cited

U.S. PATENT DOCUMENTS

| | | | |
|---|---|---|---|
| 1,520,930 | A | 12/1924 | Calhoun |
| 2,015,617 | A | 9/1935 | Claudius |
| 2,215,126 | A | 9/1940 | Mcmillin |
| 2,681,652 | A | 6/1954 | Laxton |
| 3,349,771 | A | 10/1967 | Baer |
| 3,463,149 | A | 8/1969 | Theodor |
| 3,643,660 | A | 2/1972 | Hudson |
| 3,747,597 | A | 7/1973 | Olivera |
| 3,802,431 | A | 4/1974 | Farr |
| 4,156,426 | A | 5/1979 | Gold |
| 4,231,360 | A | 11/1980 | Zloczysti |
| 4,294,243 | A | 10/1981 | Ernsting et al. |
| 4,367,735 | A | 1/1983 | Dali |
| 4,457,756 | A | 7/1984 | Kern |
| 4,592,357 | A | 6/1986 | Ersek |
| 4,648,398 | A | 3/1987 | Agdanowski |
| 4,774,935 | A | 10/1988 | Aronsohn |
| 4,859,360 | A | 8/1989 | Suzuki |
| D315,705 | S | 3/1991 | Smith |
| 5,105,807 | A | 4/1992 | Kahn et al. |
| D327,329 | S | 6/1992 | Hubbard |
| 5,218,721 | A | 6/1993 | Mathews |
| 5,336,163 | A | 8/1994 | DeMane |
| 5,383,691 | A | 1/1995 | Anthony |
| 5,383,891 | A | 1/1995 | Walker |
| 5,584,822 | A | 12/1996 | Lively |
| 5,611,333 | A | 3/1997 | Johnson |
| D385,355 | S | 10/1997 | Fabricant |
| 5,752,511 | A | 5/1998 | Simmons |
| 5,762,494 | A | 6/1998 | Archambault |
| 5,887,437 | A | 3/1999 | Maxim |
| 5,890,486 | A | 4/1999 | Mitra |
| 5,899,918 | A | 5/1999 | Knott |
| 5,922,006 | A | 7/1999 | Sugerman |
| 5,961,537 | A | 10/1999 | Gould |
| D442,285 | S | 5/2001 | Perry |
| 6,354,293 | B1 | 3/2002 | Madison |
| 6,499,140 | B1 | 12/2002 | Benjamin |
| 6,595,940 | B1 | 7/2003 | D'Alessio et al. |
| 6,666,211 | B1 | 12/2003 | Awoniyi |
| D494,671 | S | 8/2004 | Chiang |
| 6,971,387 | B2 | 12/2005 | Michaels |
| 6,971,388 | B1 | 12/2005 | Michaels |
| D522,650 | S | 6/2006 | Clawson |
| 7,055,523 | B1 | 6/2006 | Brown |
| 7,294,138 | B2 * | 11/2007 | Shippert ............ A61F 13/2005 |
| | | | 606/162 |
| D561,335 | S | 2/2008 | Pinter |
| 7,390,331 | B2 | 6/2008 | Santin |
| D576,726 | S | 9/2008 | Maxwell |
| 7,506,649 | B2 | 3/2009 | Doshi |
| D598,092 | S | 8/2009 | Agbenyega |
| 7,878,197 | B2 | 2/2011 | Christy |
| D648,489 | S | 11/2011 | Stockard |
| 8,161,971 | B2 | 4/2012 | Jaffe |
| 8,240,309 | B2 | 8/2012 | Doshi |
| D669,977 | S | 10/2012 | Chiang |
| 8,303,619 | B2 | 11/2012 | Decrescenzo |
| 8,403,954 | B2 | 3/2013 | Santin |
| 8,491,622 | B2 | 7/2013 | Brown |
| 8,604,267 | B2 | 12/2013 | East |
| D703,826 | S | 4/2014 | Nihsioka |
| D704,823 | S | 5/2014 | Rindner |
| 8,834,512 | B1 | 9/2014 | Brown et al. |
| 8,974,486 | B2 | 3/2015 | Kotler |
| D741,998 | S | 10/2015 | Martin |
| D753,821 | S | 4/2016 | Pepper et al. |

| | | | |
|---|---|---|---|
| D754,850 | S | 4/2016 | Pepper et al. |
| D759,239 | S | 6/2016 | Hartley |
| D760,373 | S | 6/2016 | Bucha |
| 9,433,808 | B2 | 9/2016 | Curtis |
| D774,648 | S | 12/2016 | Johnson et al. |
| D788,913 | S | 6/2017 | Pepper et al. |
| 9,730,830 | B2 | 8/2017 | Foley |
| D800,537 | S | 10/2017 | Harris |
| 9,775,738 | B2 | 10/2017 | Andre |
| 10,058,732 | B2 | 8/2018 | Ghosh |
| 10,143,477 | B2 | 12/2018 | Hsu |
| 10,195,088 | B2 | 2/2019 | Clayborne |
| D857,212 | S | 8/2019 | Sugaya |
| D865,200 | S | 10/2019 | Clayborne |
| D881,376 | S | 4/2020 | McCormick |
| D889,647 | S | 7/2020 | Smith |
| D893,702 | S | 8/2020 | Chiang |
| 10,736,792 | B1 | 8/2020 | Fischell |
| 10,792,059 | B2 | 10/2020 | Napolez |
| 10,792,193 | B2 | 10/2020 | Hart |
| 10,800,905 | B2 | 10/2020 | Delli-Santi |
| D903,985 | S | 12/2020 | Cannon |
| 10,980,676 | B2 | 4/2021 | Clayborne |
| D922,037 | S | 6/2021 | Bennett |
| D925,745 | S | 7/2021 | Chen |
| D932,742 | S | 10/2021 | Ruiz |
| 11,235,184 | B1 | 2/2022 | Caputy et al. |
| 11,241,271 | B2 | 2/2022 | Wolf |
| D952,141 | S | 5/2022 | Pepper et al. |
| 11,628,083 | B1 | 4/2023 | Brown |
| D1,054,025 | S | 12/2024 | Nie |
| 2002/0124844 | A1 | 9/2002 | Chiang |
| 2004/0010283 | A1 | 1/2004 | Buzard |
| 2005/0187502 | A1 | 8/2005 | Krempel |
| 2005/0288620 | A1 | 12/2005 | Shippert |
| 2006/0206120 | A1 | 9/2006 | Clawson |
| 2006/0287699 | A1 | 12/2006 | Riedle |
| 2007/0157357 | A1 | 7/2007 | Cymbol |
| 2008/0078415 | A1 | 4/2008 | Mishler |
| 2009/0007919 | A1 | 1/2009 | Dolezal |
| 2009/0149772 | A1 | 6/2009 | Macdonald |
| 2009/0277459 | A1 | 11/2009 | Al-Zeir |
| 2009/0299405 | A1 | 12/2009 | Decrescenzo |
| 2010/0125295 | A1 | 5/2010 | Wien |
| 2010/0252040 | A1 | 10/2010 | Kapust |
| 2012/0010647 | A1 | 1/2012 | Pylyp |
| 2012/0046607 | A1 | 2/2012 | Syk |
| 2012/0266346 | A1 | 10/2012 | Kessler, III |
| 2012/0330345 | A1 | 12/2012 | Tasca |
| 2013/0092173 | A1 | 4/2013 | Alexander |
| 2013/0144325 | A1 | 6/2013 | Allegra |
| 2013/0245584 | A1 | 9/2013 | Krasikoff |
| 2014/0261459 | A1 | 9/2014 | Santelli, Jr. |
| 2015/0196420 | A1 | 7/2015 | Ede et al. |
| 2015/0209228 | A1 | 7/2015 | Bruce |
| 2016/0030523 | A1 | 2/2016 | Husain |
| 2016/0030720 | A1 | 2/2016 | Husain |
| 2016/0220251 | A1 | 8/2016 | Gozar |
| 2016/0235953 | A1 | 8/2016 | Hsu |
| 2016/0296378 | A1 | 10/2016 | Phillips |
| 2016/0324679 | A1 | 11/2016 | Khan |
| 2016/0367276 | A1 | 12/2016 | Moloney |
| 2017/0172593 | A1 | 6/2017 | Hopper et al. |
| 2018/0236199 | A1 | 8/2018 | Lussier |
| 2019/0029880 | A1 | 1/2019 | Dubois |
| 2019/0167486 | A1 | 6/2019 | Clayborne |
| 2019/0290941 | A1 | 9/2019 | Chiang |
| 2019/0296378 | A1 | 9/2019 | Wang |
| 2021/0220628 | A1 | 7/2021 | Fayerberg |
| 2021/0244574 | A1 | 8/2021 | Clayborne |
| 2021/0267616 | A1 | 9/2021 | Minks |
| 2022/0080138 | A1 | 3/2022 | Pepper et al. |
| 2023/0355420 | A1 | 11/2023 | Shetye et al. |

FOREIGN PATENT DOCUMENTS

| | | |
|---|---|---|
| CN | 303290370 S | 7/2015 |
| CN | 303290371 S | 7/2015 |
| CN | 105617566 A * | 6/2016 |

(56)       References Cited

FOREIGN PATENT DOCUMENTS

| | | | | | |
|---|---|---|---|---|---|
| CN | 111388896 | A | 7/2020 | | |
| CN | 306384880 | S | 3/2021 | | |
| DE | 20215704 | U1 * | 1/2003 | .......... | A61F 13/126 |
| DE | 102009050180 | A1 | 4/2011 | | |
| FR | 030172001 | | 4/2003 | | |
| GB | 695963 | A | 8/1953 | | |
| GB | 816887 | A | 7/1959 | | |
| GB | 1511634 | | 5/1978 | | |
| GB | 2363575 | A | 1/2002 | | |
| JP | 2020014882 | A * | 1/2020 | | |
| KR | 301103344 | | 4/2021 | | |
| KR | 301108604 | | 5/2021 | | |
| KR | 102361879 | B1 | 2/2022 | | |
| WO | 2014080222 | A1 | 5/2014 | | |
| WO | 2020247470 | A1 | 12/2020 | | |
| WO | 2021150176 | A1 | 7/2021 | | |

OTHER PUBLICATIONS

"NoseAid, first aid for nosebleeds," Clever Products LLC, 2005, 1 page.

"NoseBudd helps to stop nosebleeds cold!™," Nosebudd, 2 pages.

"Rapid Rhino Controls Epistaxis", ArthroCare ENT, Rapid Rhino, 2 pages.

"The Bleed Freeze Solution," Bleed Freeze: 2015 GW Business Plan Competition Final Presentation, Youtube, published Jul. 2, 2015, 1 page.

"What is merocel material?," 1 page.

International Search Report and Written Opinion issued in PCT/US17/18141 dated May 10, 2017.

International Search report mailed Sep. 25, 2023 in corresponding PCT Application No. PCT/US2023/064753. 3 pages.

Amazon: "16 Pieces Nose Clips Stop Nosebleeds Epistaxis Clip Nose Nasal Stopper Plastic Foam for Adult Accidental Emergency," Mar. 19, 2020, 3 Pages, [Retrieved on May 16, 2025] Retrieved from URL: https://us.amazon.com/ Stopper-Plastic-Accidental-Emergency-Condition/dp/B08644YVV5F.

Amazon: "Air Max Unisex Classic Nasal Dilators Trial Pack—Anti Snoring Device for Men and Woman—Improves Airflow—1 Small—1 Medium," Apr. 26, 2013, 3 Pages, [Retrieved on May 12, 2025]

Retrieved from URL: https:// uw.amazon.com/Air-Max-Unisex-Classic-Dilators/dp/B00B4S61QE.

Amazon: "Speedo Unisex Nose Clip for Swimming Waterproof Reusable Training," Sep. 3, 2012, 3 Pages, [Retrieved on May 12, 2025] Retrieved from URL: https://www.amazon.com/ Speedo-Liquid-Comfort-Nose-Charcoal/dp/B0095KIX82.

Amazon: "RhinoPinch Nasal/Nose Clips, First Aid for Nose Bleeds (Epistaxis)—Pack of 5," Mar. 12, 2015, 3 Pages, [Retrieved on May 12, 2025] Retrieved from URL: https://www.amazon.com/ MYAID-RhinoPinch-Nasal-Bleeds-Epistaxis/dp/B00SHDPZNE.

Amazon: "Swimming Nose Clip, 14 Packs Swim Nose Plugs with Waterproof Silica Gel for Kids (Age 7+) and Adults, Multi-Color," Nov. 20, 2021, 10 Pages, [Retrieved on May 12, 2025] Retrieved from URL: https://www.amazon.com/Hurdilen-Swimming-Waterproof-Silica-Multi-Color/dp/B09M9JVLMG.

Amazon: "Zoggs Unisex Adult Silicone Swimming Nose Clip with Compact Carry Case | Easy Fit Plastic Frame, Soft Silicone Pads," Mar. 21, 2021, 6 Pages, [Retrieved on May 12, 2025] Retrieved from URL: https://www.amazon.com/Zoggs-Universal-Nose-Clip/dp/B000N8HCQY?gQT=1&th=1.

Facebook: "NasaClip", Jul. 1, 2022, 1 Page, [Retrieved on May 9, 2024] Retrieved from URL: https://www.facebook.com/NasaClip/photos/pb. 100077877690536.-2207520000/155428460361657/type=3.

International Preliminary Report on Patentability for International Application No. PCT/US2023/064753, dated Oct. 3, 2024, 8 Pages.

Linkedin: "NasaClip," Jul. 2024, 1 Page, [Retrieved on May 12, 2025] Retrieved from URL: https://www.linkedin.com/posts/ nasaclip_ nosebleedrelief-firstaidessential-nasalcare-activity-7208868583374794752-QmDN.

Minerva Health Solutions: "Rhinopinch Nasal/Nose Clips, First Aid For Nose Bleeds (Epistaxis)," May 12, 2025, 3 Pages, [Retrieved on May 12, 2025] Retrieved from URL: https://minervahealthinc.com/products/rhinopinch-nasal-nose-clips-first-aid-for-nose-bleeds-epistaxis.

Nasaclip: "N1 Metal 10pk: Single Use (Adults)—NasaClip," May 12, 2025, 6 Page, [Retrieved on May 12, 2025] Retrieved from URL: https://shop.nasaclip.com/products/n1-metal-10pk-single-use-adults.

NoseAid: "First Aid For Nosebleeds," Clever Products LLC, Facebook, 2005, 5 Pages.

* cited by examiner

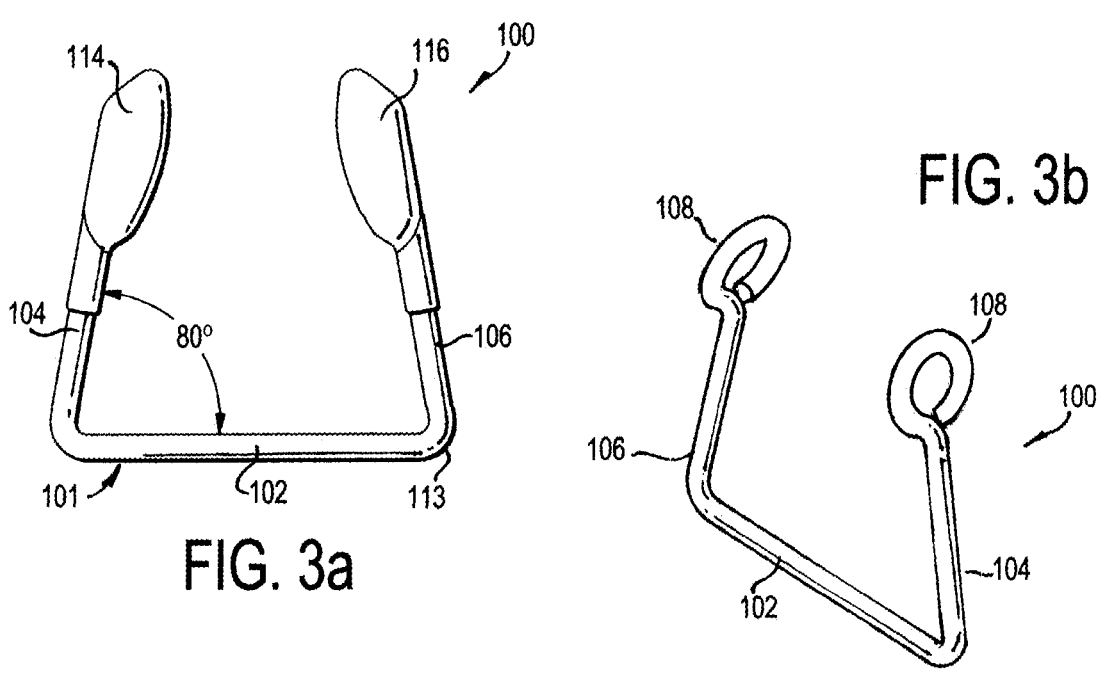
FIG. 3b
FIG. 3a
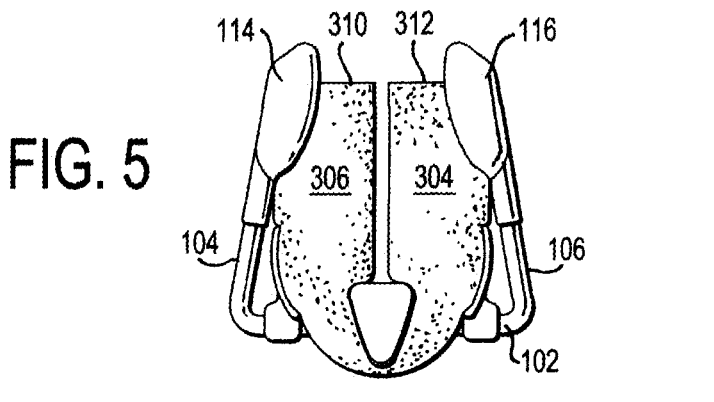
FIG. 5
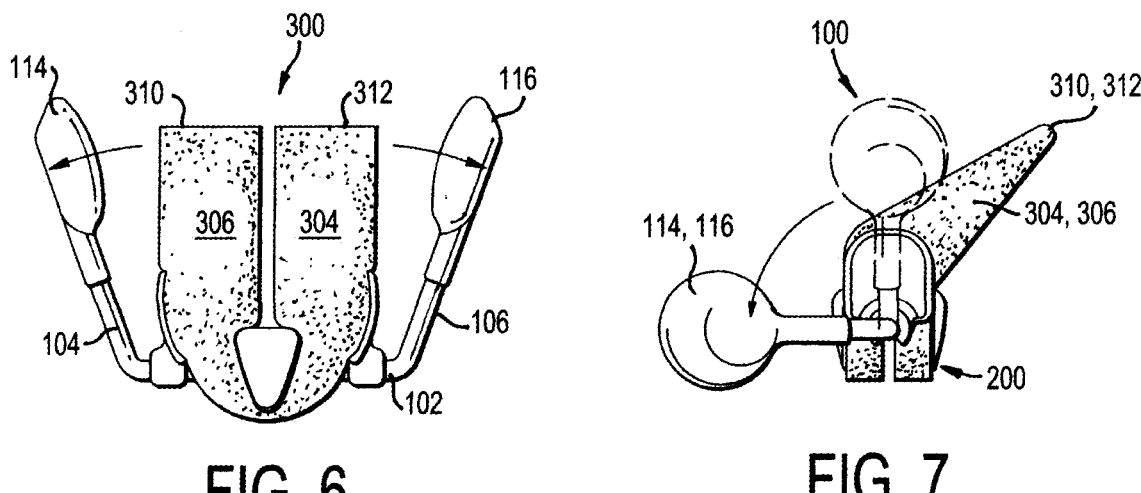
FIG. 6                    FIG. 7

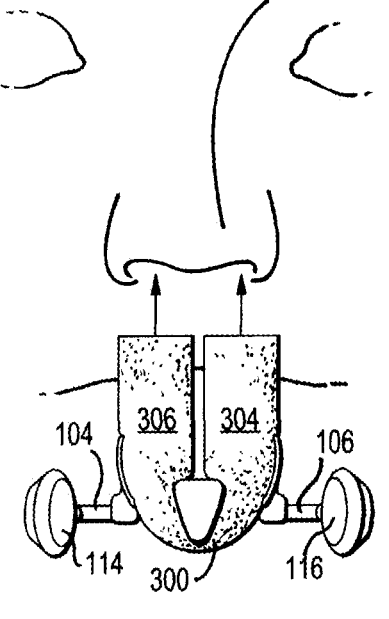
FIG. 8
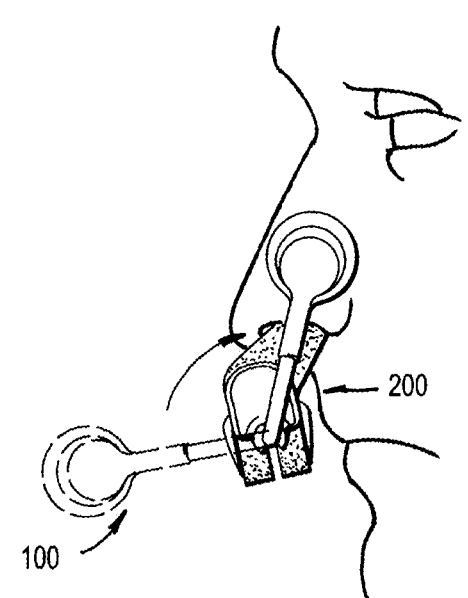
FIG. 9
FIG. 10
FIG. 11
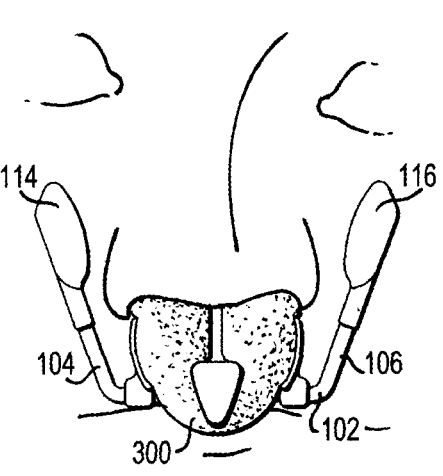
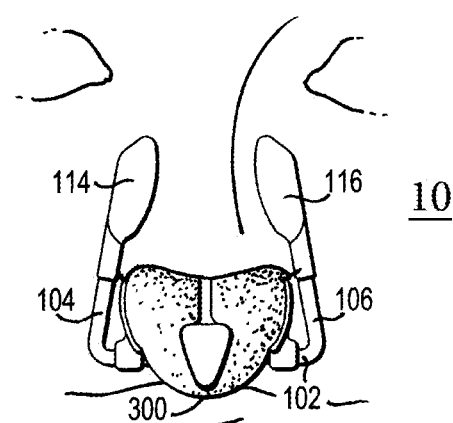

NASAL COMPRESSION DEVICE

CROSS-REFERENCE TO RELATED APPLICATIONS

This application claims the benefit of priority of U.S. Provisional Application Ser. No. 63/322,438 filed on Mar. 22, 2022, the content of which is relied upon and incorporated herein by reference in its entirety

BACKGROUND

Sixty percent of people will experience a nosebleed in their lifetime. In the United States, nosebleeds account for approximately 1 in 200 emergency department visits, which is over 500,000 visits to the emergency room in the United States annually of which nearly 90% are safely sent home. Nosebleeds are very messy, bloody, anxiety provoking experiences that could be easily managed at home if treated appropriately. Epistaxis, the medical term for nosebleed, is one of the most common ear, nose, and throat emergencies. Epistaxis has a bimodal age distribution, with most cases in children 2-10 years old and adults 50-80 years old. Certain high-risk groups, such as the elderly, require rapid intervention to stem bleeding and prevent further complications.

Nosebleeds are commonly mismanaged when they first begin. One common mistake in treating nosebleeds relates to improper compression. Nosebleeds should be treated by applying appropriate pressure to the soft side walls of the nose, for 10 to 20 minutes without interruption, and positioning the head slightly forward. While this sounds simple, it is hard to do. Another common mistake is inadequate compression time. Nosebleeds need compression for 10 to 20 minutes without interruption. Due to arm fatigue, these steps are hard to do consistently.

Medications can be used to constrict vessels to help stop bleeding. However, there is little education or awareness of how, when and what medications can be used. At home, children and elderly may easily tire, forget, or not understand these steps for successful nosebleed rescue.

SUMMARY

Accordingly, it is one object of the present disclosure to provide a device that treats nosebleeds. It is another object of the disclosure to provide a device that treats nosebleeds by applying a compression force against the lateral side surfaces of the user's nose. It is another object of the disclosure to provide a device that treats nosebleeds by inserting a sponge, absorbent material or synthetic inside the user's nasal passage. It is another object of the disclosure to provide a device that treats nosebleeds by applying a compression force against the lateral side surfaces of the user's nose at the same time it inserts a sponge inside the user's nasal passage. It is a further object of the disclosure to provide a nose compression device that can be used hands-free and that does not obstruct the user's mouth and/or eyes and can be used with a surgical mask.

A nose compression device for treating a nosebleed of a person. The device includes a wire frame having a straight middle section and two end sections angled with respect to the middle section. The device also has a support member attached to the wire frame, and a single continuous nasal sponge with opposing ends. The sponge is attached to the body for insertion into the person's nasal passages. The wire frame is pliable so that the end sections can be moved between an opened position and a compression position. In the opened position, the end sections are spread apart to be wider than the user's nose, and the device is slid upward on the user's face so that the nasal sponges enter the user's nasal passages. The end sections are then pressed inward into the compression position to a pinch position where they pinch the lateral side surfaces of the user's nose (the ala) at a constant pressure (sufficient to stop air or fluid flow) for an extended period of time (10 to 20 minutes). In the compression position, the end sections are pressed inward so that they are at an acute angle with respect to the middle section. The nasal sponges can be pre-treated with medication and/or materials to further stop the nosebleed.

This summary is not intended to identify all essential features of the claimed subject matter, nor is it intended for use in determining the scope of the claimed subject matter. It is to be understood that both the foregoing general description and the following detailed description are exemplary and are intended to provide an overview or framework to understand the nature and character of the disclosure.

BRIEF DESCRIPTION OF THE FIGURES

The accompanying drawings are incorporated in and constitute a part of this specification. It is to be understood that the drawings illustrate only some examples of the disclosure and other examples or combinations of various examples that are not specifically illustrated in the figures may still fall within the scope of this disclosure. Examples will now be described with additional detail through the use of the drawings, in which:

FIG. 3(a) is a plan view of the wire frame with a pinch pad;

FIG. 3(b) is a plan view of the wire frame with the pinch pad removed for illustrative purposes;

FIG. 5 is a top view of the nasal compression device with the support arms moved inward to the compression position;

FIG. 6 is a top view of the nasal compression device with the support arms moved outward to the opened position;

FIG. 7 is a side view of the nasal compression device with the support member rotated about the frame member so that the nasal sponges are unobstructed by the support arms;

FIG. 8 is a top view of the nasal compression device being inserted into the nasal passage of a user;

FIG. 9 is a side view of the nasal compression device with the support member rotated about the frame member so that the support arms extend along the side surface of the user's nose;

FIG. 10 is a top view of the nasal compression device with the support arms outward to the opened position to align the nasal compression device on the user's nose;

FIG. 11 is a top view of the nasal compression device with the support arms pressed inward to the compression position to exert a compression force on the side surface of the user's nose.

Figures 1, 2, 4A, 4B:
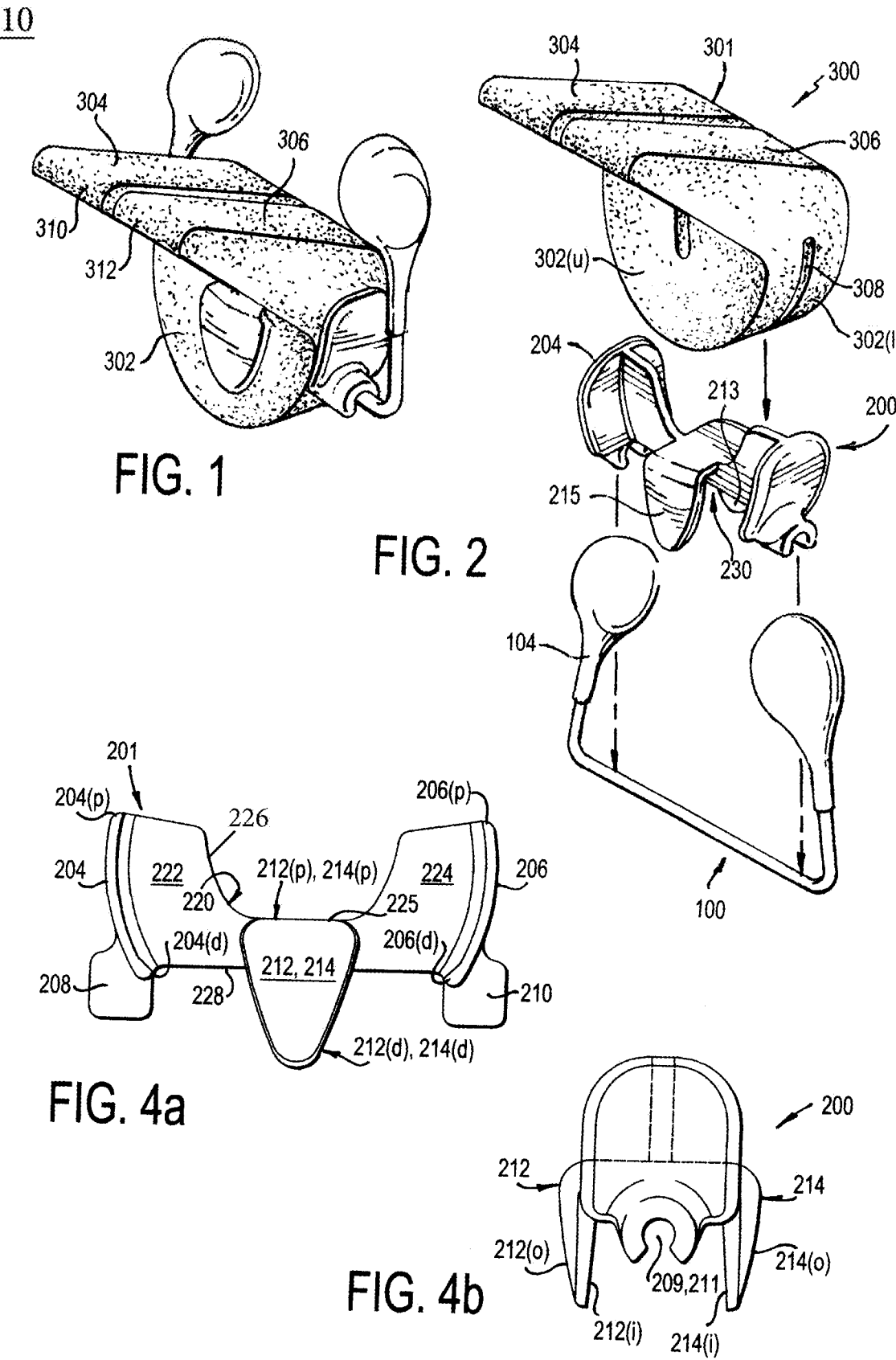
FIG. 1 is a perspective view of the nasal compression device in accordance with an embodiment of the disclosure.
FIG. 2 is an exploded perspective view of the nasal compression device.
FIG. 4(a) is a top view of the support member.
FIG. 4(b) is a side view of the support member.

The figures show one illustrative embodiment of the present disclosure. Other embodiments can have components of different scale. Like numbers used in the figures may be used to refer to like components. However, the use of a number to refer to a component or step in a given figure has a same structure or function when used in another figure labeled with the same number, except as otherwise noted.

DETAILED DESCRIPTION

In describing the illustrative, non-limiting embodiments illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several embodiments are described for illustrative purposes, it being understood that the description and claims are not limited to the illustrated embodiments and other embodiments not specifically shown in the drawings may also be within the scope of this disclosure.

Turning to the drawings, FIGS. 1-11 show a nasal compression device 10 in accordance with one illustrative non-limiting example of the disclosure. As best shown in FIG. 11, the device 10 is designed to treat anterior epistaxis or nosebleeds. Referring to FIGS. 1-4, the device may include a frame member 100 having external pressure members formed by end sections or side portions that form arms 104, 106 and pinch pads 114, 116, a support member 200, and an internal applicator or internal member 300.

The support member 200 couples the internal member 300 to the frame member 100, and positions the internal member 300 with respect to the external pressure members 104, 106. The external pressure members 104, 106 provide an inward pressure against the outer surface of the nasal passage to pinch the nasal passage closed and seal any broken nasal blood vessel. At least a portion of the internal member 300 may contact the inner surface of the nasal passage and any broken nasal blood vessel to further seal any broken nasal blood vessel. In some embodiments, the internal member 300 may release liquid medication when the device is squeezed shut and facilitate distribution over nasal mucosa where bleeding originates (e.g., Kiesselbach's plexus).

Frame Member 100

As best shown in FIGS. 3(a), 3(b), the frame member 100 has a body 101 that may be, for instance, an elongated flexible wire. The wire 101 may have a central portion 102, and two side portions or arms 104, 106. Each arm 104, 106 extends outward from an opposite end of the central portion 102, so that the central portion 102 is positioned between the two side arms 104, 106. The central portion 102 and each arm 104, 106 is substantially straight, and have a curved corner or bend 113 therebetween. Each arm 104, 106 has a respective distal end portion 108.

Figure 12A:
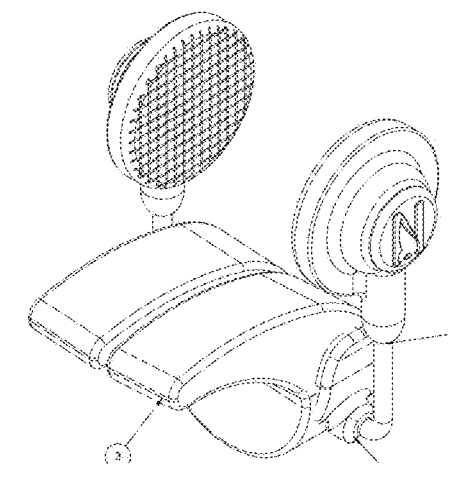
FIGS. 12(a)-(e) illustrate another embodiment of the nasal compression device.
Figure 12B:
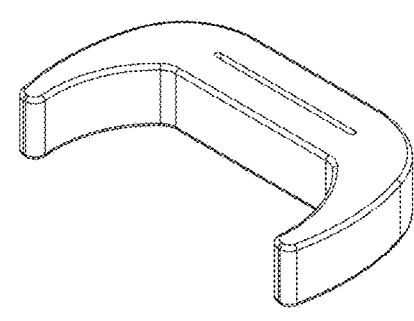
Figure 12C:
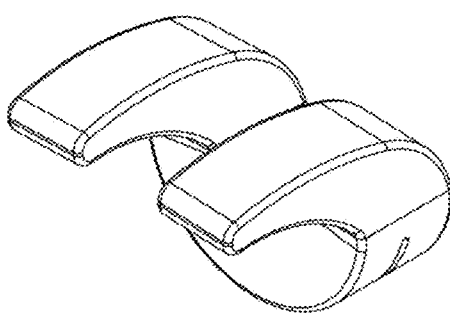
Figure 12D:
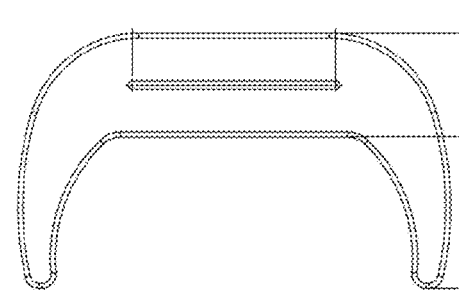
Figure 12E:
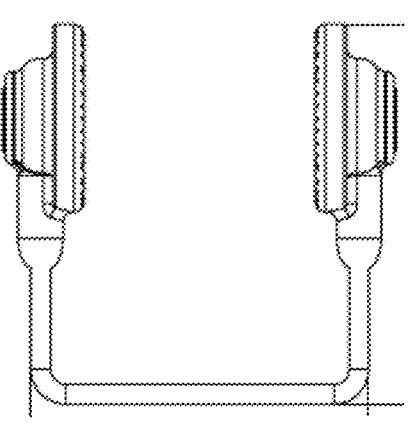

The body 101 is flexible at the bends 113 so that the side arms 104, 106 can be moved inwardly and outwardly with respect to each other, between an opened position and a closed or compression position. In the opened position, the side portions 104, 106 are positioned outwardly so that they are wider than the user's nasal passage, as shown in FIGS. 6, 10. In the compression position, the side portions 104, 106 are positioned inwardly to compress against the user's nasal passage, as shown in FIGS. 5, 11, 12(e). In this manner, the central portion 102 and side arms 104, 106 form a general U-shape.

Thus, one or both of the arms 104, 106 can be moved inwardly by the user into the compression position or a pinch position. For instance, the user may simultaneously (or separately) press inwardly on the arms 104, 106 and/or on the outside of the pinch pads 114, 116 to bend the corners 113 so that the pinch pads 114, 116 at the distal ends of the side arms 104, 106 move inward toward each other and toward the internal members 300, so that each arm 104, 106 is at an acute angle with respect to the central portion 102. However, the pinch pads 114, 116 at the distal ends do not touch one another. In one example embodiment, the arms 104, 106 can be at an angle of approximately 60-80 degrees with respect to the central portion 102. The arms 104, 106 stay in the compressed position until changed by the user.

In addition, the arms 104, 106 can be moved outwardly by the user into the opened position. For instance, the user may simultaneously (or individually) pull outwardly on the arms 104, 106 and/or on the inside or outside of the pinch pads 114, 116 to bend the corners 113 of the frame 100 so that the pinch pads 114, 116 at the distal ends of the arms 104, 106 move outward away from each other and away from the internal members 300. In the opened position, each arm 104, 106 is at a larger angle than the closed position, and in some embodiments at a right or obtuse angle (90-120 degrees) with respect to the central portion 102. The arms 104, 106 stay in the opened position until changed by the user. That is, at all positions, the arms 104, 106 are not biased to the closed position or the opened position, and do not have any spring force. Rather, the arms 104, 106 stay fixed in the position that the user sets. Accordingly, the frame arms 104, 106 and pinch pads 114, 116 are adjustable by the user, and the inward pressure is adjustable. That is, the user can set the frame arms 104, 106 and pinch pads 114, 116 to a desired adjustable position to achieve a desired adjustable pressure by pressing the frame arms 104, 106 inward until that position and pressure is achieved. For example, if the user has a slight nosebleed, only a slight pressure might be needed. If the user has a severe nosebleed, the user can set a greater pressure. And, the user can direct the device so that the pinch pads 114, 116 align with the location of the nosebleed inside the nasal passage.

As shown in FIG. 3(b), the distal end portion 108 of each arm 104, 106 can optionally be configured to provide a structure that may readily be coupled with a respective pinch pad 114, 116. For instance, the distal end portion 108 may form a partially or completely closed circle shape at the distal end of the arms 104, 106. The circular shape provides an expanded surface area for the pinch pads 114, 116, so that the pinch pads 114, 116 can be more readily and reliably fitted to the distal end portions 108.

The entire frame member 100 (including the central portion, arms 104, 106, and distal end portion 108) is formed as a single unitary and continuous member. The frame 100 may be formed in any suitable manner, including CNC wire-forming using an aluminum alloy, molded shape, polymer or metal. Preferably, however, the frame member 100 has sufficient rigidity to apply a constant, appropriate and effective inward pressure on the outer nose when in the closed position and stay in the closed position when located on the user's nose. Still in further embodiments, the frame 100 can be a shape memory polymer that is cold activated.

Support Member 200

Referring to FIGS. 2, 4(a), and 4(b), the support member 200 of the device 10 is shown. The support member 200 may be formed as a clipping or attachment mechanism having a body 201 that includes a central support platform 220, a first side support 204, a second side support 206, a first internal member engagement feature 212, a second internal member engagement feature 214, a first frame coupling device 208 and a second frame coupling device 210. The body 201 may have a semi-circular shape with a bottom side and a top side.

The central support platform 220 has a first side portion forming a first wing 222, a second side portion forming a second wing 224, and a center or intermediate portion 225 formed between the first side portion and the second side portion. The entire central support platform 220, including the first and second side portions and the intermediate portion 225, are formed as a single unitary member and is a thin plate. The first and second wings 222, 224 are substantially wider than the intermediate portion 225 and the wings 222, 224 and intermediate portion 225 together form a continuous curved trailing or inner edge 226 that has a general U-shape. The wings 222, 224 have respective proximal ends where the inner edge 226 is angled slightly inward. The central support platform 220 also has an outer or leading edge 228 that is substantially straight. The inner edge 226 is at an inner portion or proximal end of the platform 220 and the outer edge is at an outer portion or distal end of the platform 220.

The first and second side supports 204, 206 extend orthogonally outward from the wings 222, 224 in both directions, so that the wings 222, 224 are approximately centered on the side supports 204, 206 to form a T-shape cross-section. The first and second side supports 204, 206 are thin plates and are curved to provide an ergonomic shape, and have a proximal end 204(p), 206(p) and a distal end 204(d), 206(d). The two outer proximal corners of the device 10, at the inner edge 226 at the proximal side support 204(p), 206(p) are curved. The inner edge 226 is angled slightly inward from the proximal ends 204(p), 206(p) of the side supports 204, 206. The side supports 204, 206 have a curved inner surface that receive and support the outer surface of the nasal sponge 300 when the sponge 300 is engaged with the support member 200.

The first and second internal member engagement features 212, 214 are positioned at the intermediate portion 225 of the support platform 220, and centered on the device 10. As best shown in FIG. 4(b), the first internal member engagement feature 212 extends from a first side (the upper surface in the embodiment shown) of the support platform 220, and the second internal member engagement feature 214 is at the opposite second side (the lower surface in the embodiment shown) of the support platform 220.

The internal member engagement features 212, 214 have a post member 213, a tab member 215, a proximal end 212(p), 214(p) and an opposite distal end 212(d), 214(d). As best shown in FIGS. 2, 4(a), the post members 213 are positioned at the proximal ends 212(p), 214(p) of the respective engagement features 212, 214, and are coupled along the inner platform portion of the support platform 220, e.g. at a portion of the inner edge 226. The post members 213 project substantially orthogonally outward from opposite outer surfaces of the intermediate platform portion 225. The tab members 215 then project substantially orthogonally outward from each of the post members 213 and outward with respect to the central platform 220 beyond the outer edge 228 of the central platform 220. Thus, the tab members 215 extend substantially parallel to the central support platform 220, at the intermediate portion 225, and extend from the inner proximal end and inner edge 226 toward and beyond the outer distal end and leading edge 228. And, as best shown in FIGS. 2, 4(b), a channel 230 is formed between the intermediate platform portion 225 and the tab members 215, and particularly the inner surfaces 212(i), 214(i) of the tab members 215.

In addition, the tab members 215 have a general triangular shape with rounded corners, with the base aligned along the inner edge 226 of the support platform 220 at the proximal end 212(p), 214(p) and the tip extending outward from the support platform 220 at the distal end 212(d), 214(d). Each tab 215 has an inner surface 212(i), 214(i) and an outer surface 212(o), 214(o). It is noted that while two engagement features 212, 214 are shown, only a single engagement feature can be utilized. And, the engagement features 212, 214 need not be comprised of a post 213 and a tab member 215, but can be any suitable engagement feature such as a fastener and/or adhesive.

The first and second frame coupling devices 208, 210 are positioned at opposite sides of the body 201, at the distal end 204(d), 206(d) of the side supports 204, 206, respectively, at the leading corners of the body 201 where the side supports 204, 206 meet the outer edge 228. In addition, the first and second frame coupling devices 208, 210 are positioned at about the middle of the body 201, i.e., substantially aligned with the central support platform 220 and the middle of the side supports 204, 206. In the exemplary embodiment shown in FIG. 4(a), the first frame coupling device 208 is aligned with the first side support 204, and the second frame coupling device 210 is aligned with the second side support 206.

In the example embodiment shown in FIG. 4(b), the first and second frame coupling devices 208, 210 are formed outward with respect to the side supports 204, 206 and the central platform 220. Thus, the coupling devices 208, 210 can rotatably engage the central portion 102 of the frame 100 without obstruction, and the frame central portion 102 extends substantially parallel to the leading edge 228 and between the two tab members 212, 214, as best shown in FIGS. 2, 5. As some embodiments, as further shown in FIGS. 4(a), 5, the distal tab ends 212(d), 214(d), extend beyond the coupling devices 208, 210.

Returning to FIG. 4(b), the coupling devices 208, 210 have a C-shaped cross-section with a gap between the distal ends forming a mouth and a receiving channel 209, 211. The first and second frame coupling devices 208, 210 snap onto the frame 100. In particular, the central portion 102 of the frame 100 is pressed into the channel 209, 211 of the coupling devices 208, 210. The distal ends of the coupling devices 208, 210 are smaller than the diameter of the frame central portion 102, so that the frame central portion 102 snaps into the coupling devices 208, 210 and are reliably retained in the channels 209, 211 until the user forcibly uncouples them by pulling apart.

In addition, the coupling devices 208, 210 are rotatably coupled to the frame central portion 102, so that the support member 200 can be rotated with respect to the frame 100. Once the frame 100 is coupled to the support member 200, it remains in position. The user can rotate the support member 200 with respect to the frame 100 and the coupling devices 208, 210 maintain that position. The clip is sufficiently strong to provide enough friction between the clip and the frame to prevent the support member 200 from inadvertently rotating with respect to the frame central portion 102. The support member 200 can be removed by the user forcing the support member 200 apart from the frame 100 and pulling the frame 100 outward with respect to the support member 200. It will be appreciated that other suitable couplings can be provided between the frame 100 and the support 200, such as by use of a fastener, and/or adhesive. In some embodiments, the support 200 can be removed from the frame 100 so that different size supports 200 or frames 100 can be provided or replaced. In addition, though two coupling devices 208, 210 are shown, only a single coupling device can be provided, or more than two coupling devices can be provided.

As best shown in FIGS. 1, 2, 5, the support member 200 is fixedly coupled to the internal member 300. In turn, the support member 200 rotatably and removably couples the internal member 300 to the frame 100 and to the external pressure members formed by the arms 104, 106 and the pinch pads 114, 116. Thus, the device 10 provides both internal and external pressure members in a single unit. Or, the support member 200 can be removed from the frame 100 so that the user can utilize only the internal member 300 or the external pressure members, depending on a particular application.

The support member 200 is formed as a single unitary and continuous member, such as by extrusion. Accordingly, the central support platform 220, side supports 204, 206, engagement features 212, 214, and coupling devices 208, 210 form a single unitary piece. In addition, the support member 200 may be made of a plastic that is rigid but allows the coupling devices 208, 210 to flex slightly due to the small amount of material where the coupling devices 208, 210 connect to the central frame portion 102. The support member 200 may be made from plastic polymers, metal, foam or combination materials to help with traction and comfort. The support member 200 can be formed as a discrete member, as shown, or can be integral with the frame 100. The body 201 may have one or more internal or external surfaces with edges, ridges or material to help the user grip the body 201.

External Pressure Members 114, 116

Referring to FIGS. 1, 2, 3(*a*), 5-11, external pressure members 114, 116 are attached to the distal end portion 108 (FIG. 3(*b*)) of the frame member 100. For instance, the external pressure members 114, 116 may be nasal pinch pads, such as soft material made of silicone or other soft material to apply constant no-slip pressure to the soft part of the nose on either side. The pads 114, 116 are sufficiently thick and soft to be comfortable to a user, but also sufficiently rigid to apply sufficient pressure to the nose to stop bleeding. The pads 114, 116 can be molded directly to the distal end portion 108 of the frame 100, and may surround the circle and/or a portion of the arms 104, 106. In one embodiment, the surface of the pinch pad 114, 116 can be roughened or cross-hatched to better grip the user's nose, as illustrated in FIG. 12(*a*).

Accordingly, a pinch pad 114, 116 is located at the distal end portion 108 of each side arm 104, 106 and each has a rounded shape that conforms to the outer surface of the user's nasal passage. The pads 114, 116 can be relatively flat to maximize the amount of surface area that contacts the nasal passage and apply the maximum inward pressure. The pinch pads 114, 116 are a plastic material that is extruded over the distal end portions of the side arms 104, 106. The pads 114, 116 are sufficiently rigid to apply an inward pressure to the outer surface of the user's nasal passage, and also protect the user against injury, such as any sharp surfaces of the frame member 100. In one embodiment, the frame 100 is a wire frame with a silicone over-mold or a silicone/plastic material for the pinch pads 114, 116. The pinch pads 114, 116 can have a shape that is circular, oval, triangular or tear drop.

In an alternative embodiment, the pads 114, 116 can have an internal opening that has a shape which matches the distal end portion 108 of the frame 100. Accordingly, the user can removably attach the pads 114, 116 to the distal frame portion 108 by sliding the distal frame portions 108 into the opening inside the pads 114, 116. Of course, other suitable connections can be provided between the pads 114, 116 and the frame 100. For instance, the pads 114, 116 can be adhered, strapped or fastened to the frame 100, and no opening or recess need be provided in the pads 114, 116.

The pads 114, 116 are soft and malleable so that it conforms to the shape of the nose. Thus, pressure may be controlled by the force exerted by the user to apply enough pressure to stop bleeding but the user can control the force to gauge for comfort. The pads 114, 116 and the entire device 10 can be made in various dimensions to fit an adult, child or different sized noses.

Internal Member 300

Referring to FIGS. 1, 2, 12(*a*)-(*d*), an internal member 300 is provided that attaches to the support member 200. The internal member 300 has a body 301 with a central portion 302 and two opposing arms 304, 306. The central portion 302 has a general U-shape (FIGS. 12(*b*), 12(*d*)), with the arms 304, 306 extending in the same direction forward from the central portion 302. The arms 304, 306 are elongated and tapered with a wider proximal end at the central portion 302 and taper outward to a narrower distal end with a distal tip 310, 312, respectively. The arms 304, 306 extend at about 20-60 degrees to the central portion 302, and in one embodiment about 30 degrees to the central portion 302, as best shown in FIG. 7. And, as shown in FIG. 5, the internal member arms 304, 306 are slightly shorter than the frame arms 104, 106, though in other embodiments the internal member arms 304, 306 can be shorter, longer or the same length as the frame arms 104, 106.

Referring to FIGS. 2, 12(*b*), (*d*), a transverse slit or slot 308 is located in the central portion that extends completely through the middle of the central portion 302 to form an upper half central portion 302(*u*) and a lower half central portion 302(*l*). The slot 308 extends transversely and is parallel to the top and bottom surfaces of the internal member 300.

Thus, the first and second arms 304, 306 of the internal member 300 are each configured to be shaped and sized to fit in a person's nose. Each arm 304, 306 is inserted into each nare before the external pressure members (i.e., the frame arms 104, 106 and the pinch pads 114, 116) are pinched in place. Once the internal member 300 is inserted into the nasal passage, they compress flat when pinched which is more comfortable in the nose. In some embodiments, the internal member 300 (or at least the distal ends that extend inside the nose) can be saturated with a medication prior to insertion. When the internal member 300 is squeezed, it compresses to release medication or absorbs and provides some internal tamponade. For example, the internal member 300 can release the medication in the nasal mucosa so that liquid comes in contact with areas of bleeding.

In one exemplary embodiment, the internal member 300 may be a nasal sponge and can be made for instance of foam, sponge, dehydrated sponge like materials, and can optionally be presoaked with medication (and optionally dehydrated). The internal member 300 can be biocompatible foam that absorbs blood and/or induces clot formation or hemostasis. The primary purpose of the sponge is to deliver medication, but the sponge can also provide an expanding absorbent material that provides internal tamponade, or can be configured to exert a pressure against the nose to stop bleeding. In addition, the nasal sponges 300 may be made out of absorbable polymers, sponges or other material that can be combined or coated with zinc oxide, bacitracin or antibiotic ointment in addition to analgesic and vasoconstrictive medications such as but not limited to oxymetazoline, epinephrine, phenylephrine, pseudoephedrine, lidocaine or tranexamic acid (TXA).

As shown in FIGS. 7-9, the arms 304, 306 of the sponge 300 extend upward upon entry and then posterior into the nare, while the base of the arms 304, 306 may project slightly out of the nasal passage at the exterior of the nose. The nasal sponge arms 304, 306 fit securely below the nose but above the level of the upper lip to be comfortably positioned in the nasal passages, and can be readily inserted into and withdrawn from the nasal passages. The sponge arms 304, 306 can easily slide into the nare and quickly and easily release pre-soaked medication to mucous membranes inside the nasal shaft. They do not adhere to or disrupt scab formation. The sponge 300 and sponge arms 304, 306 can be provided in different sizes, shapes and angles to fit different ages (nose size) and internal nose shapes.

The entire internal member 300 is formed as a single unitary piece, including the central portion 302 and the arms 304, 306. This provides better placement within the nasal passage, and easier removal from the nasal passage after use since the central portion 302 assists with removal of the sponge arms 304, 306. In addition, the one piece ensures that the internal member 300 doesn't detach and become lodged/stuck in the nare or nasal passage. In one embodiment, the internal member 300 is a one-piece sponge. However, in other embodiments, the internal member 300 can be two or more pieces that are separately held in position by separate support or attachment members such as a fastener or adhesive that are made of a different material than the internal member 300, such as plastic or metal, and can be rigid or flexible. In some embodiments, the top surface (which forms the bottom surface when the arms are folded together, as in FIGS. 1-2, 7-11) of the arms 304, 306 are straight (FIGS. 1, 2), though in other embodiments, the top surface is curved (FIGS. 12(*a*)-(*d*)).

Assembly

The frame 100, support member 200 and internal member 300 are discrete and separate from one another. To assemble the device 10, the internal member 300 is initially positioned on the support member 200. To do so, the arms 304, 306 of the internal member 300 are folded up (compare FIG. 12(*b*) and FIG. 2) so that the arms 304, 306 to come together with both of the arms 304, 306 facing in the same direction. The central sponge portion 302 is aligned with the central support platform 220. The central sponge portion 302 and central support platform 220 have a similar shape, so that the central sponge portion 302 fits about the central support platform 220. The thin central support platform 220 slides into the slot 302 between the upper sponge portion 302(*u*) and the lower sponge portion 302(*l*). If needed, the user can separate the upper sponge portion 302(*u*) from the lower sponge portion 302(*l*) to facilitate entry into the slot 302.

The user then lifts and pulls one of the upper or lower sponge portions 302(*u*), 302(*l*) over the top of the respective tab member 215 and beyond the distal end 212(*d*), 214(*d*) of the tab member 215. The user then pushes the sponge portions 302(*u*), 302(*l*) down below the tab member 215 and into the channel 230. At least a portion of the central sponge portion 302 is received in the channel 230 under the tab member 215, and a portion of the central sponge portion 302 can extend beyond the tab member 215 to avoid injury if the user otherwise contacts the tab 215 or outer edge 228 during use.

Once the sponge 300 is in position, the upper sponge portion 302(*u*) rests on the outer surface of the top surface of the central support platform 220, and the lower sponge portion 302(*l*) rests on the outer surface of the lower surface of the central support platform 220. The side supports 204, 206 support the outer sides of the internal member 300 during insertion into the nasal passage to add stability to the sponge arms 304, 306 and facilitate insertion.

At this point, the internal member 300 is reliably attached to the support member 200 and cannot come free during normal use of the device 10. The support member 200 is then rotatably coupled to the frame 100 by snapping the frame coupling devices 208, 210 onto the central portion 102 of the frame 100. Medication can optionally be placed on the internal member 300, and sealed within a bag to prevent the medication from escaping or evaporating. The frame 100 can be coated in plastic so that it does not rust or chemically interact or interfere with the medication, for instance a skin-safe plastic dip. In one embodiment, the wire frame is at least partly anodized and has a silicone pinch pad, though the wire doesn't come in contact with the skin. The support member 200 is made of plastic or material so that it does not chemically interact or interfere with the medication.

The device is now fully assembled and ready for use. In some embodiments, the device is fully preassembled so that the user (e.g., medical practitioner or patient) need not assemble the device 10. In addition, the device 10 can be disposable after a single use. In some embodiments, the device 10 can be reused by removing and discarding the internal member 300 after use, cleaning the support member 200 and frame 100, and placing a new internal member 300. The sponges can be checked after 10-20 minutes, rinsed with clean water and reinserted for a total of 30 minutes, though other times can be utilized. The support member 200 is removed from the frame 100 by pulling them apart. And the internal member 300 is removed from the support member 200 by the reverse operation, namely by pulling the central portion 302 past the distal end of the tab member 215 out of the channel 230, and sliding it off of the support platform 220.

Overall Operation

Operation of the device 10 will be discussed with respect to FIGS. 5-11. The frame member 100 of the device 10 is moved from the closed position (FIG. 5) to the open position (FIG. 6). If needed, the user can move the arms 104, 106 outwardly in the direction of the arrows, to provide an appropriate separation. In the open position, the side arms 114, 116 are substantially orthogonal or at an obtuse angle with respect to the middle portion 102 (though in some embodiments the side arms 114, 116 can be slightly smaller than orthogonal). Thus, the distal ends 108 and pinch pads 114, 116 are wider apart than the user's nose so that the user can insert the nasal sponge arms 304, 306 into the user's nasal passages by moving the side frame 100 upward (and posteriorly) along the external lateral side surface of the user's nose.

Referring to FIG. 7, the device is placed in an insertion position to prepare the device for insertion into the user's nose. The user rotates the frame arms 104, 106 with respect to the support member 200, and away from the sponge arms 304, 306, in the direction of the arrow as shown. This moves the arms 104, 106 and pinch pads 114, 116 away from the user and the distal ends 310, 312 of the sponge arms 304, 306. Accordingly, the sponge arms 304, 306, and particularly the distal ends 310, 312 are free of the frame arms 102, 104 and the pinch pads 114, 116, so that the frame arms 102, 104 do not interfere with insertion of the sponge arms 304, 306 into the nasal passage of the user.

Turning to FIG. 8, the user then inserts the distal ends 310, 312 of the sponge arms 304, 306 into the user's nasal passage in the direction of the arrows shown. In FIG. 9, the sponge arms 304, 306 are inside the user's nasal passage, and apply an outward pressure to stop bleeding. At this point, the frame arms 104, 106 and pinch pads 114, 116 are facing away from the user, as shown. The user then moves the device 10 into a pre-pinch position. The user rotates the frame arms 104, 106 with respect to the support member 200 (as shown by the arrows), so that the pinch pads 114, 116 come up alongside the outside of the user's nasal passage, as shown in FIG. 10.

In FIG. 11, the user places the device 10 in the closed position. The user presses inward on the frame arms 104, 106 or pinch pads 114, 116 until the pinch pads 114, 116 engage the user's nasal passage. In the pinch position, the frame arms 104, 106 are positioned inward so that the distal end portion 108 is narrower than the normal width of a user's nose. In that position, the arms 104, 106 are at an acute angle with respect to the middle portion 102. The pinch pads 114, 116 apply an inward pressure to help stop the nosebleed. The pinch pads 114, 116 will remain in that position and apply constant pressure for up to 30 minutes or more, until bleeding has stopped, and the user need not manually hold the device 10 in position. The arms 104, 106 remain in that pinched position until separated by the user for removal from the nose by separating the arms 104, 106 outwardly.

As shown in FIGS. 9-11, in the pinched position, the support member 200 and the central portion 102 of the frame member 100 are positioned at the patient's upper lip directly below the nostrils and septum. The frame arms 104, 106 extend upward on the patient along the lateral surface of the nose. The distal frame ends 108 are positioned at the lateral surface of the nose, so that the external pads 114, 116 apply pressure at a proper position to stop the nosebleed. The frame arms 104, 106 exert an inward force so that the pinch pads 114, 116 apply an inward pressure or pinch force against the lateral surface of the nose, while at the same time the sponge arms 304, 306 are positioned inside the nose and applying an outward force. The nasal pads 114, 116 thereby apply pressure to the ala (soft side walls of the nose). The pinch force can be controlled by adjusting the amount of inward pressure applied by the frame arms 104, 106, so that enough force is applied to control the bleeding, but without exerting too much force to cause pain or damage the user's nose.

As shown in FIG. 11, once the device 10 is positioned on the nose, it is hands-free since it remains in place on the user's nose by itself due to the inward pinch force once the frame arms 104, 106 are bent to the inward pinch position, and without the user having to hold it in position. The device 10 remains in position until the user separates the frame arms 104, 106 and then withdraws the nasal sponge 300 from the user's nasal passage. Thus, the device 10 (i.e., distal end portions 108 and pads 114, 116) pinches the lateral side surfaces of the user's nose, and simultaneously stops bleeding through delivery of vasoconstrictive medications applied by the nasal sponge 300. Of course, the device 10 need not have both the pinch pads 114, 116 and the nasal sponge 300. For instance, the sponge 300 (and support member 200) can be removed, so that only a pinching force is applied by the distal end portion 108 and pads 114, 116.

In an alternative embodiment of the present disclosure, the frame member 100 may be inwardly spring biased, whereby the arms 104, 106 are positioned inwardly in the closed position when at rest and may be separated outwardly by the user to be in the open position. In the open position, the device 10 may be placed over the user's nose, and when the user releases the arms 104, 106, they return to the inward position to apply a pressure to the nose.

According to this alternative embodiment, the pinch position may be the normal position for the device 10 when it is at rest. To place the device 10 on the user's nose, the device 10 is moved to the open position whereby the frame arms 104, 106 are forced apart against the inward bias force. That can be performed, for instance, by pulling outward on the frame arms 104, 106 and/or the pinch pads 114, 116. The nose sponge 300 is then positioned inside the user's nasal passage and the pinch pads 114, 116 are simultaneously positioned along the exterior lateral surface of the nose. The frame arms 104, 106 are then released, so that they move inward and return to the pinch position. In that pinched position, the nasal pads 114, 116 exert a pinching force.

The vast majority of nosebleeds occur in the anterior part of the nose and from the nasal septum. This area contains many blood vessels from Kiesselbach's plexus, also known as Little's area. The nasal compression device 100 is designed to control bleeding via direct compression on the outer nose, by placing pressure directly over Kiesselbach's plexus, in combination with vasoconstriction from sponge inserts soaked with oxymetazoline or other vasoconstricting medication or hemostatic agent possible with some analgesic ingredient such as lidocaine and/or antibacterial agent such as bacitracin. The device 10 may also be designed to come in multiple sizes to fit adults and children.

The device can be made available in several sizes, such as child, teen, and adult. Each size may have, for instance, a different width (e.g., by varying the length of the central portion 102), a different height (e.g., by varying the length of the frame arms 104, 106). The different sizes can also have different sizes of nasal pads 114, 116 and nasal sponge arms 304, 306.

CONCLUSION

The device 10 provides a safe, effective and low-cost solution to nosebleed emergencies. The device comes in adjustable sizes and applies constant hands-free pressure to the soft side walls of the nose, incorporates intranasal sponges to control bleeding, and is designed to apply a constant adequate pressure to the nose for the appropriate amount of time (e.g., 10-20 minutes). The device can also utilize medication that further controls bleeding by constricting bleeding vessels and improves the success of hemorrhage control.

In some embodiments, the device 10 need not be used to compress the nose to stop a nosebleed, but instead can be utilized for other purposes and applications, for example, to deliver medications by placing the medication on the arms 304, 306 of the internal member 300, such as analgesic, allergy medications, benzodiazepines, naloxone or other medications that can be applied intranasally. This is especially useful in an emergency or other situations where IV access or taking pills cannot be well tolerated, such as for conditions other than nosebleeds. In those embodiments, the arms 304, 306 and pinch pads 114, 116 need not be positioned to compress the nose to stop a nosebleed, but apply a lighter pressure to remain in place as the medication is delivered via the arms 304, 306 of the internal member 300.

The present device 10 provides value to three different customer segments: medical providers, sports medicine professionals and parents, caretakers or individuals who suffer from frequent nosebleeds. For medical providers, this device can reduce the time needed by medical professionals to effectively manage common nosebleeds. For coaches, trainers and school nurses, this device is easy to use and effective for nosebleed emergencies. For parents and caretakers, the device is the comfortable, safe, low-cost solution to nose-bleed rescue that can reduce or eliminate costly visits to the emergency room or doctor's office.

The device is available in adjustable sizes and applies constant hands-free pressure to the soft side walls of the nose, incorporates cooling to help constrict vessels to control bleeding, and is designed to automatically apply adequate pressure to the nose for 10-20 minutes. The device also uses medication that further controls bleeding by vaso-constriction and improves the success of hemorrhage control.

The device is a safe, effective and simple to use device that can be placed on the patient by a nurse, an emergency room clinician or family member and does not require constant supervision by a medical professional. It allows providers to effectively manage epistaxis with minimal cost, time or repeated attempts and helps to facilitate throughput which reduces length of stay, an important hospital bench-mark. These advantages make the present device attractive not only to the beneficiary, the patient, but also to the hospital or physician who recommends use of the product.

The device is easy to use, stops bleeding immediately and has step-by-step instructions for managing nosebleeds. It is a device that any trainer or first aid station would want to have on hand for disposable, immediate and effective treatment for nosebleed emergencies. Any customers who are prone to nosebleeds would be attracted to the low price, intuitive design, effectiveness and comfort. The device provides easy step-by-step instructions to apply constant pressure to the correct part of the nose with the added value of including medication which increases the success of bleed-ing control and potentially prevents unnecessary visits to the doctor's office or emergency room. Currently, there are no devices on the market that use this combination of technique and medication to treat nosebleed emergencies. The device is valuable because it provides cost savings, effective man-agement and ease of use to (1) medical providers/physicians, (2) school and sports professionals and (3) direct to con-sumer customer segments and by preventing prolonged nosebleeds it avoids overutilization and expense to the health care system.

The device 10 is adjustable for comfortable fit to the contour of the nose, since the nasal pads 114, 116 are soft and malleable and with applied pressure conforms to the shape of the nose. As set by the user, it applies the appro-priate amount of pressure in the appropriate location at the soft side walls of the nose, hands-free. It is positioned completely below or to the side of the nose, and does not extend upward above the soft side walls of the nose. Thus, it does not obstruct vision or line of sight of the user's eyes. It also does not extend below the upper lip, so that it does not obstruct the user's mouth and can be used with a surgical mask.

It is noted that the device 10 as shown and described is configured for simultaneous use on both nostrils. However, the device 10 can be configured so that only one nostril is treated, such as by providing one internal member arm and one respective external pressure member 104, 106 and 114, 116. In addition, the device can be used without the internal member 300; for example, the pinch pads 114, 116 can be used by itself. The device 10 is designed for hands-free application of a constant pressure that the person experienc-ing the nosebleed can apply alone without the assistance of another person or a medical technician. In addition, while the device 10 has been described for use to stop nosebleeds, it can be used for other purposes; for example, the device can be a medication applicator that administers a medication to a patient and the pinch pads optionally provides only suf-ficient pressure on the nose to keep the device positioned on the nose.

In one embodiment, the nasal sponge is one piece and die cut, the support member 200 is injection molded, the frame 100 is aluminum/iron wire which is bent into the desired shape and has a silicone overmold. The components include the medical grade open cell intranasal sponge that can have a liquid or gel medication added to, the sponge is one piece that slips over a PVC plastic base that clips onto the wire and allows for rotation of the sponge at the base of the wire, the aluminum/iron wire (or any type of metal/plastic) can be pulled apart and then pinched shut to hold pressure per user's needs and the silicone (or other plastic) pinch pads that provide compressible but comfortable pressure over the nostrils preventing any leakage of air or fluid. It will further be appreciated that any suitable materials can be used for the device, other than those disclosed, such as for the clip wire or plastic/silicone pinch pads, and provide constant pressure on the nostrils. In addition, other structures can be utilized to provide constant pressure on the nostrils within the spirit and scope of the disclosure.

The manufacturing process includes bending of the wire into a U shape with a coil at the end which has a silicone (or other plastic) over-mold, the inner pinch pad is textured to provide grip when applied against the user's nostrils. The PVC plastic base is injection molded, the nasal foam (one piece) contains a slit that allows it to slip over and load on the plastic base which then has clips that allow it to attach to the base of the clip and rotate the sponge as needed. This piece can be removed (e.g., for users aged 2-5) who may not tolerate the nasal sponges. The entire device can then be packaged in a track and vacuum sealed shut.

It will be apparent to those skilled in the art having the benefit of the teachings presented in the foregoing descrip-tions and the associated drawings that modifications, com-binations, sub-combinations, and variations can be made without departing from the spirit or scope of this disclosure. Likewise, the various examples described may be used individually or in combination with other examples. Those skilled in the art will appreciate various combinations of examples not specifically described or illustrated herein that are still within the scope of this disclosure. In this respect, it is to be understood that the disclosure is not limited to the specific examples set forth and the examples of the disclo-sure are intended to be illustrative, not limiting.

It is noted that the drawings may illustrate, and the description and claims may use geometric or relational terms, such as upper, lower, side, top, bottom, curved, straight, elongated, parallel, orthogonal, triangular, circular, etc. These terms are not intended to limit the disclosure and, in general, are used for convenience to facilitate the descrip-tion based on the examples shown in the figures. In addition, the geometric or relational terms may not be exact. For instance, walls may not be exactly perpendicular or parallel to one another because of, for example, roughness of sur-faces, tolerances allowed in manufacturing, etc., but may still be considered to be perpendicular or parallel.

Reference is made herein to some "embodiments." It should be understood that an embodiment is an example of a possible implementation of any features and/or elements presented in the attached claims. Some embodiments have been described for the purpose of illuminating one or more of the potential ways in which the specific features and/or elements of the attached claims fulfill the requirements of uniqueness, utility, and non-obviousness.

What is claimed is:

1. A nose compression device for use on a person, the device comprising:

a wire frame having a straight middle section and two side sections angled with respect to the middle section to apply an inward compression against an outside of the person's nose;

a support member attached to the wire frame;

a single nasal sponge attached to the body and having a central sponge portion and two opposing sponge end portions, each of said two opposing sponge end portions configured for insertion into the person's nasal passages, said support member comprising a thin support platform receiving the central sponge portion; and a sponge engagement feature configured to attach to the central sponge portion of said single nasal sponge wherein said sponge engagement feature comprises a post extending orthogonal to said thin support platform and a tab extending from said post to form a channel, wherein said nasal sponge is received in the channel.

2. The device of claim 1, said support member further comprising a snap feature rotatably attached to the wire frame.

3. The device of claim 1, said device having an insertion position whereby the two side sections are rotated with respect to the support member to face away from the user as the user inserts the two opposing end portions into the person's nasal passages.

4. The device of claim 3, said device having a post-insertion position whereby the two side sections are rotated with respect to the support member to align along a side of the person's nasal passages.

5. The device of claim 4, said device having a pinch position whereby the two side sections are pressed inwardly toward each other to pinch the person's nasal passages.

6. The device of claim 1, the two opposing sponge end portions being substantially orthogonal to the central sponge portion.

7. The device of claim 1, wherein the middle section can be positioned below the person's nose and the two side sections extend upward along opposing lateral side surfaces of the person's nose.

8. The device of claim 1, wherein each of said side sections have a distal end, and further comprising a pinch pad attached to the distal end.

9. The device of claim 8, wherein the pad extends upward along the lateral surface of the user's nose.

10. The device of claim 1, wherein said two opposing end portions of said nasal sponge contain a medication.

11. The device of claim 10, wherein the medication is a vasoconstrictive medication or an analgesic medication, and/or an antibacterial agent.

12. The device of claim 10, wherein the medication comprises one or more of oxymetazoline, epinephrine, phenylephrine, pseudoephedrine, lidocaine, tranexamic acid, lidocaine, zinc oxide, and bacitracin or other medications that perform similar actions.

13. The device of claim 1, wherein said two side sections are flexible and moveable between a pinch position where the two side sections are at an acute angle to the middle section and an open position where the two side sections can be moved outward with respect to the middle section.

14. The device of claim 1, wherein in the open position the two side sections are orthogonal or obtuse with respect to the middle section.

15. The device of claim 1, wherein the device does not obstruct the person's eyes or mouth.

16. A nose compression device for use on a person, the device comprising:

a wire frame having a straight middle section and two side sections angled with respect to the middle section to apply an inward compression against an outside of the person's nose;

a support member attached to the wire frame, a single nasal sponge attached to the body and having a central sponge portion and two opposing sponge end portions, each of said two opposing sponge end portions configured for insertion into the person's nasal passages;

a slot in the central sponge portion defining an upper central sponge portion and a lower central sponge portion, said support member having a thin platform received in the slot between the upper and lower central sponge portions.

17. The device of claim 16, said support member further comprising a snap feature rotatably attached to the wire frame.

18. The device of claim 16, said device having an insertion position whereby the two side sections are rotated with respect to the support member to face away from the user as the user inserts the two opposing end portions into the person's nasal passages.

19. The device of claim 18, said device having a post-insertion position whereby the two side sections are rotated with respect to the support member to align along a side of the person's nasal passages.

20. The device of claim 19, said device having a pinch position whereby the two side sections are pressed inwardly toward each other to pinch the person's nasal passages.

21. The device of claim 16, the two opposing sponge end portions being substantially orthogonal to the central sponge portion.

22. The device of claim 16, wherein the middle section can be positioned below the person's nose and the two side sections extend upward along opposing lateral side surfaces of the person's nose.

* * * * *